US012622676B2

(12) United States Patent
Baumann et al.

(10) Patent No.: US 12,622,676 B2
(45) Date of Patent: May 12, 2026

(54) DEVICE FOR PERFORMING ULTRASONIC EXAMINATIONS AND PRESSURE MEASUREMENTS

(71) Applicant: Compremium AG, Muri b. Bern (CH)

(72) Inventors: Ulrich Baumann, Münsingen (CH); Vincent Boris Baumann, Gümligen (CH); Peter Nuot Frei, Dulliken (CH)

(73) Assignee: COMPREMIUM AG, Bern (CH)

( * ) Notice: Subject to any disclaimer, the term of this patent is extended or adjusted under 35 U.S.C. 154(b) by 102 days.

(21) Appl. No.: 18/697,683

(22) PCT Filed: Oct. 26, 2022

(86) PCT No.: PCT/EP2022/079972
§ 371 (c)(1),
(2) Date: Apr. 1, 2024

(87) PCT Pub. No.: WO2023/104390
PCT Pub. Date: Jun. 15, 2023

(65) Prior Publication Data
US 2025/0228527 A1      Jul. 17, 2025

(30) Foreign Application Priority Data
Dec. 9, 2021     (CH) ................................. 70688/2021

(51) Int. Cl.
*A61B 8/00*          (2006.01)
(52) U.S. Cl.
CPC .............. *A61B 8/485* (2013.01); *A61B 8/429*
(2013.01)

(58) Field of Classification Search
CPC ....... A61B 8/485; A61B 8/429; A61B 8/4416;
G01L 9/0048; G01L 19/003;
(Continued)

(56) References Cited

U.S. PATENT DOCUMENTS 6,511,427 B1 *    1/2003   Sliwa, Jr. ............... A61B 8/429
600/459
2008/0058644 A1 *  3/2008   Sandrin ................ A61B 8/4209
600/459

(Continued)

FOREIGN PATENT DOCUMENTS

EP           1 415 596 A1    5/2004
WO     WO 2018/187340 A1   10/2018

OTHER PUBLICATIONS

EP 1 415 596 A1; Machine Language English Translation.

*Primary Examiner* — Bo Joseph Peng
(74) *Attorney, Agent, or Firm* — Lerner David LLP

(57)          ABSTRACT
A device (1) for performing ultrasonic examinations and pressure measurements comprises an ultrasonic transducer (60), a pressure sensor (50), a housing (10) to accommodate the ultrasonic transducer (60) and the pressure sensor (50), a support plate (40) arranged in the housing (10) and a flexible membrane (21) arranged on the end face of the housing. A sealed chamber (47) for receiving a liquid medium is formed between the membrane (21) and the support plate (40), and the ultrasonic transducer (60) and the pressure sensor (50) are arranged on the support plate (40) in such a way that a first transmission surface of the ultrasonic transducer (60) and a second transmission surface of the pressure sensor (50) are directed towards the chamber (47).

15 Claims, 3 Drawing Sheets

(58) Field of Classification Search
CPC . G01L 19/0038; G01L 19/143; G01L 9/0045;
G01L 9/0091; G01L 9/0041; G01L
19/0092; G01L 19/147; G01L 2019/0053
See application file for complete search history.

(56) References Cited

U.S. PATENT DOCUMENTS

| | | | |
|---|---|---|---|
| 2013/0338509 A1* | 12/2013 | Nakamura | H10N 30/308 |
| | | | 600/459 |
| 2015/0112199 A1* | 4/2015 | Nakamura | G01H 11/08 |
| | | | 600/459 |
| 2020/0315583 A1* | 10/2020 | Baumann | A61B 8/4281 |

* cited by examiner

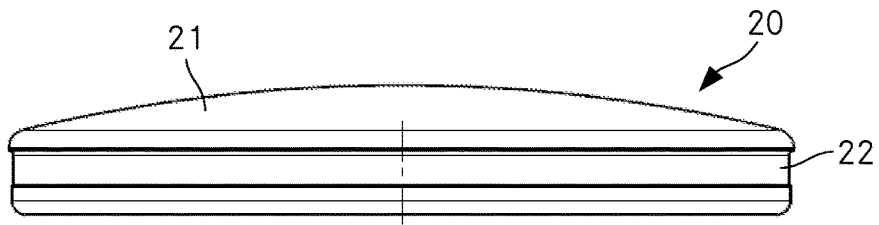
Fig. 5A
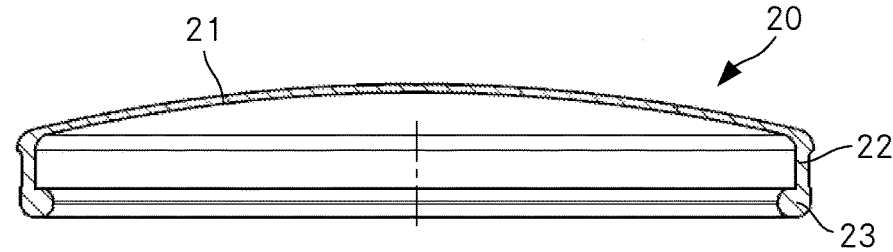
Fig. 5B
Fig. 6A
Fig. 6B

DEVICE FOR PERFORMING ULTRASONIC EXAMINATIONS AND PRESSURE MEASUREMENTS

TECHNICAL FIELD

The invention relates to a device for performing ultrasonic examinations and pressure measurements. It also relates to a method for assembling such a device.

TECHNICAL BACKGROUND

Sonography is a well-established imaging technique for examining organic tissue in medicine and veterinary medicine. An ultrasound probe is commonly used, which is guided over the surface of the body. The probe comprises an ultrasound transducer for generating ultrasound waves, for example by means of a piezo array. These are coupled into the human or animal body via an end face of the ultrasound probe. The reflected signals are in turn recorded by the ultrasonic transducer, and the depths of the reflecting tissue structures can be determined based on the transit time of the reflected signals. The desired image data can then be processed from this, with the brightness of the image information being determined on the basis of the echo signals.

It is known to perform ultrasonic examinations while the examined tissue is subjected to different external pressures. This allows the elastic properties of the examined tissue and/or the internal pressure in vessels, such as blood vessels, to be examined. In this context, hand-held devices comprising an ultrasound probe and a device for measuring pressure have already been proposed.

For example, CH 707 046 A2 (VeinPress GmbH) describes a pressure measuring device that is used together with an ultrasonic measuring unit, whereby the pressure measuring device comprises a container for an ultrasound-transparent measuring liquid that has at least two ultrasound-permeable windows. The actual pressure sensor is coupled to the accommodation volume with the measuring liquid. The container is formed, for example, by an annular housing section that surrounds the front surface of the ultrasonic measuring unit. The pressure in the container can be increased by means of a pressure generating device.

WO 2019/106535 A1 (U. Baumann, V. Baumann) describes a pressure measuring device for measuring the pressure and/or elasticity of a vein, an organ or a compartment and for combination with an ultrasound measuring unit. It comprises a pressure sensor designed as a foil pressure sensor, whereby a space between the foils of the foil pressure sensor is filled with an ultrasound-transparent and non-electrolytically active liquid. The pressure measuring device is placed on the body surface in the area of the tissue to be examined, the ultrasonic measuring unit then interacts mechanically with the back of the pressure measuring device and the ultrasonic waves are transmitted through the pressure measuring device.

Handling two separate units is cumbersome. The publication therefore also suggests coupling the pressure measuring device mechanically to the body surface or to the ultrasound measuring unit. The latter is done, for example, by means of an L-shaped adapter that can be attached to the housing of the ultrasonic measuring unit.

This solution allows easier handling, but is structurally complex and has a number of optical interfaces from the ultrasound transducer to the tissue under examination, which can negatively affect the optical quality of ultrasound imaging.

DESCRIPTION OF THE INVENTION

The object of the invention is to create a device for performing ultrasonic examinations and pressure measurements, which belongs to the technical field mentioned at the beginning, which is simple in design and enables a high imaging quality.

The solution to the problem is defined by the features of claim 1. According to the invention, the device for performing ultrasonic examinations and pressure measurements comprises:

a) an ultrasonic transducer;

b) a pressure sensor;

c) a housing to accommodate the ultrasonic transducer and the pressure sensor;

d) a support plate arranged in the housing; and e) a flexible membrane arranged at the front of the housing.

A sealed chamber for receiving a liquid medium is formed between the membrane and the support plate, and the ultrasonic transducer and the pressure sensor are arranged on the support plate in such a way that a first transmission surface of the ultrasonic transducer and a second transmission surface of the pressure sensor are directed towards the chamber.

Ultrasonic transducers convert alternating electrical voltage into mechanical vibrations and vice versa. They are usually based on piezo crystals arranged in a so-called array (ultrasonic array, piezo array). In the context of the invention, this array is now arranged at the support plate and is suitable for emitting and receiving ultrasonic waves into and through the chamber.

The pressure sensor is suitable for measuring an essentially static pressure prevailing in the chamber, which results in particular from the pressure force of the device on an object under investigation, e. g. a region of the body of a human or animal.

Preferably, the front main surface of the support plate facing the chamber is flat, but this is not mandatory; in principle, it can also have convex and/or concave sections.

The ultrasonic transducer and the pressure sensor can be arranged on the support plate in such a way that their transmission surfaces (which are formed, for example, by the respective end face or form part thereof) are flush with a front main surface of the plate. However, the front or measuring surface can also protrude from the front main surface. The measuring surface of the pressure sensor can be arranged behind the front main surface, i. e. set back. In the case of the ultrasonic transducer, such an arrangement must ensure that the emission and reception of the ultrasonic vibrations is not obstructed. Preferably, the first transmission surface of the ultrasonic transducer is positioned in front of the main front surface. In particular, the distance between the planes is 0.5-1.5 mm.

In particular, the housing forms a handle so that the device can be used in the manner of a conventional ultrasonic probe, whereby the pressure is also applied manually to the surface of the object being examined. The housing thus has a circumference of approx. 12-20 cm in a handle area, for example. Its cross-section can be round, oval or, for example, rectangular with rounded edges. The housing can be made of different materials. Dimensionally stable plastics, e. g. ABS plastics or polyamide, have proven to be suitable.

The support plate is made of a mechanically stable and corrosion-resistant material, at least on the side facing the chamber, e. g. anodized aluminum is suitable.

The membrane is ultrasound-permeable and is preferably made of such a flexible material that external forces are transmitted directly to the chamber behind it, so that no significant energy has to be expended to deform the membrane when the usual impact forces are applied during examinations carried out with the device. A comparatively soft membrane with a hardness of 50 Shore A or less, in particular 45 Shore A or less, ensures that a sufficiently large area of the membrane is in contact with the object to be examined even at low contact forces, so that the ultrasonic waves can be reliably transmitted between the device and the object to be examined. Silicone rubber is a particularly suitable material for the membrane. The thickness of the membrane in its active, front area, which is used for contacting the object to be examined, is ideally 0.3-0.7 mm, in particular 0.4-0.6 mm.

The membrane can form the contact surface with the object being examined, or it can be covered by another flexible, ultrasound-permeable element during the examination, e. g. by a replaceable, sterile cap for single-use or single-patient use, which ensures hygienic conditions when examining patients.

In addition to the membrane and the support plate, other components may be involved in sealing the chamber, such as specific seals or elements of the housing.

The integration of both sensors in a common chamber enables a compact design of the device according to the invention and a simple and therefore easy-to-clean outer shape. The defined interaction of the ultrasonic transducer and the pressure sensor with the housing, the support plate, the membrane and the liquid medium contained in the chamber results in a high level of process reliability.

Preferably, the membrane has a circular base. The base surface extends perpendicular to a longitudinal axis of the device. This results in an isotropic deformation of the membrane, regardless of the angle of the impact force in relation to the longitudinal axis, which is particularly important if the device is placed on the area to be examined at an angle to the longitudinal axis. Behind the membrane base surface, the element with the membrane can have further sections which are formed in one piece with the actual membrane or as further elements and are used, for example, for holding and/or sealing against the housing and/or the support plate. Like the actual membrane, these additional sections can have a circular base or a different, e. g. polygonal, geometry.

In the filled state, the active front area of the membrane in each diametrical cross-section has, in particular, a shape that corresponds to that of a chain function. This geometry results when the membrane is prestressed due to the filling of the contact liquid if the membrane has a circular base area, it is made of the same material over its entire surface in the active area and the membrane thickness is constant in this area, provided that the membrane is attached to other elements of the device in such a way that no non-radial prestressing is generated in its active area. Preferably, the membrane is preformed, i. e. its shape changes only slightly when it is filled.

In a preferred embodiment, a retaining ring interacts with a peripheral retaining area of the support plate and encloses a proximal retaining section of the membrane and holds it to the support plate.

To form the sealed chamber, the retaining ring is therefore advantageously slid over the membrane and attached to the support plate after the flexible membrane has been attached to the support plate.

The retaining ring also preferably has a circular shape, but other geometries are also possible in principle, adapted to the geometry of the membrane and the support plate. In a circular design, the retaining section can interact with the support plate via threads, i. e. the retaining ring can be designed as a screw ring. However, a bayonet or clip connection between the retaining ring and support plate is also possible, for example.

In a preferred embodiment of this type, the membrane in the retaining section has a bead that interacts with a circumferential groove in the support plate, which is arranged distally in front of the retaining area.

In particular, due to the elasticity of the material, the bead of the membrane can be guided over an end face of the support plate until it enters the groove along its entire circumference. In the area of the bead, unintentional detachment of the membrane from the support plate can be prevented by the retaining ring surrounding the corresponding section of the membrane on the outside. In this case, once the membrane has been attached to the support plate, the retaining ring is guided over the bead area of the membrane on the outside and secured to the support plate.

Advantageously, a proximal section of the retaining ring interacts with a shell-side region of the housing, in particular in the manner of a clip connection. The clip connection is formed in particular by interacting projections on the retaining ring and on the housing, at least one of the projections being conical in cross-section so that the sections can be easily attached to one another but cannot be easily detached from one another again.

The clip connection can be created easily and does not require any rotational movement between the retaining ring and the housing, for which a certain distance between the retaining ring and the proximal retaining section of the membrane would be necessary.

In a preferred embodiment of the device according to the invention, the membrane is therefore held on the support plate with the ultrasonic transducer and the pressure sensor, while the connection between the support plate with the membrane on the one hand and the housing on the other is created by the retaining ring connected to both assemblies.

In the assembled state, a circumferential seal is advantageously arranged between the proximal section of the retaining ring and the shell-side area of the housing. The circumferential seal is formed in particular by an O-ring or an annular molded seal, which is partially accommodated in a circumferential groove in the shell of the housing. Alternatively or additionally, the seal can be made between the housing and the support plate. In particular, the seal compensates for different thermal expansions if the housing and the retaining ring or the support plate are made of different materials, for example the housing is made of plastic and the retaining ring and the support plate are made of a metallic material, and thus reliably prevents the ingress of moisture or dust.

The ultrasonic transducer is preferably attached to the center of the support plate, and the pressure sensor is attached off-center on the support plate.

The ultrasonic transducer is therefore arranged in the area of the center in order to enable the best possible emission and absorption of ultrasonic waves. In the case of a circular support plate, the center of the transducer in particular essentially coincides with the center of the circle. A typical, elongated ultrasonic array, for example, extends equally far from the center of the circle in two diametrical directions, preferably up to the edge area of the support plate; the diametrical extent of the array is preferably at least 0.8 D, where D is the outer diameter of the support plate. The pressure sensor is arranged off-center in such a way that the function of the ultrasonic transducer is not impaired. Due to the isotropic distribution of the static pressure in the liquid in the chamber, the exact positioning of the pressure sensor has no influence on its measurement precision.

Advantageously, the ultrasonic transducer and the pressure sensor are each accommodated in a through-opening of the support plate, whereby the through-openings with the accommodated ultrasonic transducer and pressure sensor are sealed against the passage of the liquid medium.

The seal between the respective through-opening and the corresponding component can be created by one or more sealing elements and/or by a material-locking seal, e. g. a bond. The use of sealing compounds is also possible in principle. In a preferred embodiment, the pressure sensor is inserted from the rear into a through opening that has a support flange in the area of the end face of the support plate. A first, axial sealing element is arranged between the end face of the pressure sensor and the support flange, and a second, radial sealing element is accommodated in an outer groove of the outer surface of the pressure sensor and interacts with the inner surface of the through opening. For this purpose and in order to ensure a secure mechanical mounting of the pressure sensor housing, the through opening is formed by a tube-like section that extends axially to the rear starting from the end face of the support plate. As a consequence, in this embodiment, the pressure sensor is mechanically attached to the support plate via a holder that presses it axially forwards onto the axial seal and that is screwed to the rear of the support plate.

The ultrasonic transducer is preferably inserted into the passage opening from the front and mechanically and sealingly connected to the support plate via a sealing adhesive bond.

To use the device according to the invention, the chamber is filled with an ultrasonically transparent liquid. Advantageously, the ultrasonically transparent liquid is an oil with a viscosity in a viscosity class of 32-68 ISO VG. In particular, the oil can be a synthetic, mineral and/or vegetable oil. The viscosity is determined in accordance with DIN ISO 3448: 2010.

To introduce the liquid medium into the chamber, the device advantageously has a filling opening for the liquid medium, which is designed as a through-opening in the support plate. The chamber can thus be completely formed and sealed—with the exception of the through-opening—before filling with the medium.

Advantageously, a circuit board for holding electronic components is attached to a rear side of the support plate, and a main surface of the circuit board extends substantially perpendicular to a main surface of the support plate. The circuit board can also be supported at other locations, in particular with its rear section on the inside of the housing.

The device according to the invention is preferably assembled using a method comprising the following steps:
a) Inserting, sealing and fastening the ultrasonic transducer and the pressure sensor in the support plate;

b) Inserting a filling hose into the support plate;
c) Attaching the flexible membrane to the support plate to form the sealed chamber;
d) Filling the liquid medium into the chamber through the filling hose.
e) Closing a filling opening for the liquid medium as soon as a predetermined quantity of the medium has been filled in.

The process steps a)-c) do not necessarily have to be carried out in the specified order. The quantity of the medium can be specified directly via its mass or volume or via an internal pressure that is to be achieved in the chamber.

Further advantageous embodiments and combinations of features of the invention result from the following detailed description and the entirety of the patent claims.

BRIEF DESCRIPTION OF THE DRAWINGS

The drawings used to illustrate the embodiment example show:

FIG. 5A, B a side view and a cross-sectional view of the membrane element of the device; and FIGS. 6A and 6B a top view and a bottom view of the support plate of the device, respectively.

In principle, identical parts are marked with identical reference signs in the figures.

WAYS TO CARRY OUT THE INVENTION

Figure 1:
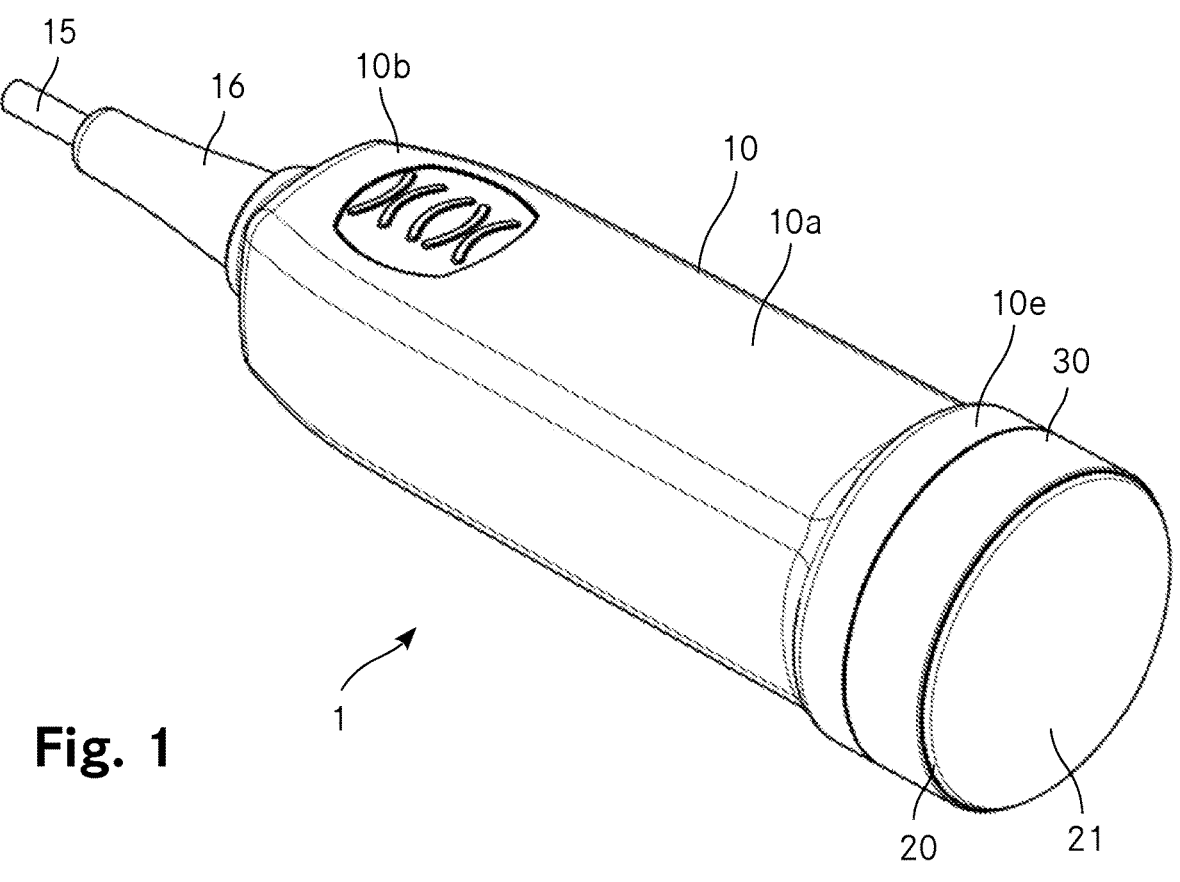
FIG. 1 An oblique view of an embodiment of a device according to the invention for carrying out ultrasonic examinations and pressure measurements.

FIG. 1 is an oblique view of an embodiment of a device according to the invention, the measuring unit 1, for carrying out ultrasonic examinations and pressure measurements. The measuring unit 1 comprises an elongated housing 10 made of ABS plastic with a wall thickness of 2.3 mm. It comprises a main part 10a, which has an essentially rectangular cross-section with rounded corners transverse to the longitudinal axis and is designed in this section so that a user can easily grasp and hold it with one hand. In a rear part 10b, the cross-section of the housing 10 tapers down to an end wall 10c of the housing 10 (see also FIG. 2). An opening is recessed in this end wall 10c, through which a cable 15 runs, protected by a strain relief 16. In a front part 10d, the housing shape merges into a connection ring 10e. To this, a membrane element 20 with a membrane 21 is attached to the front of the housing 10 via a retaining ring 30, as described in detail below.

Figure 2:
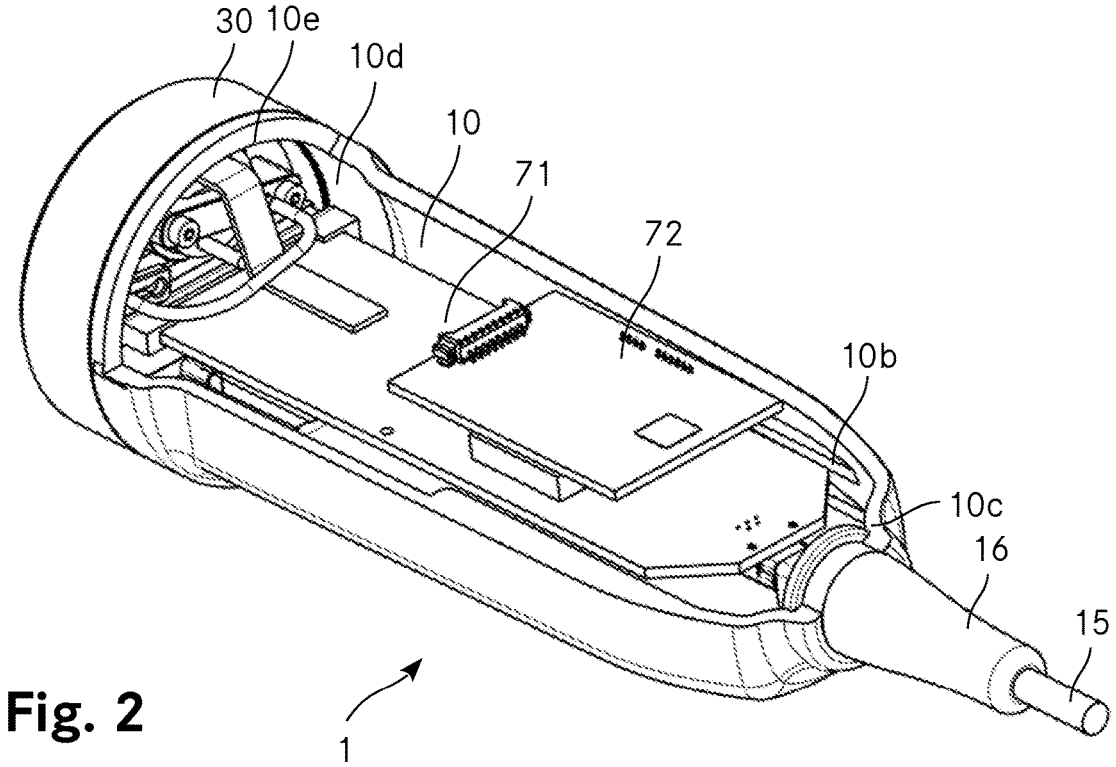
FIG. 2 another oblique image of the device, with the housing shown transparent.

As can be seen in FIG. 2, in which the housing 10 is shown transparently, a first printed circuit board 71 (mainboard) and a second printed circuit board 72 (piggyback) are accommodated in the housing 10. The first printed circuit board 71 extends essentially over the entire length of the housing 10, while the second printed circuit board 72 only requires part of the housing length.

Figures 3, 4A, 4B:
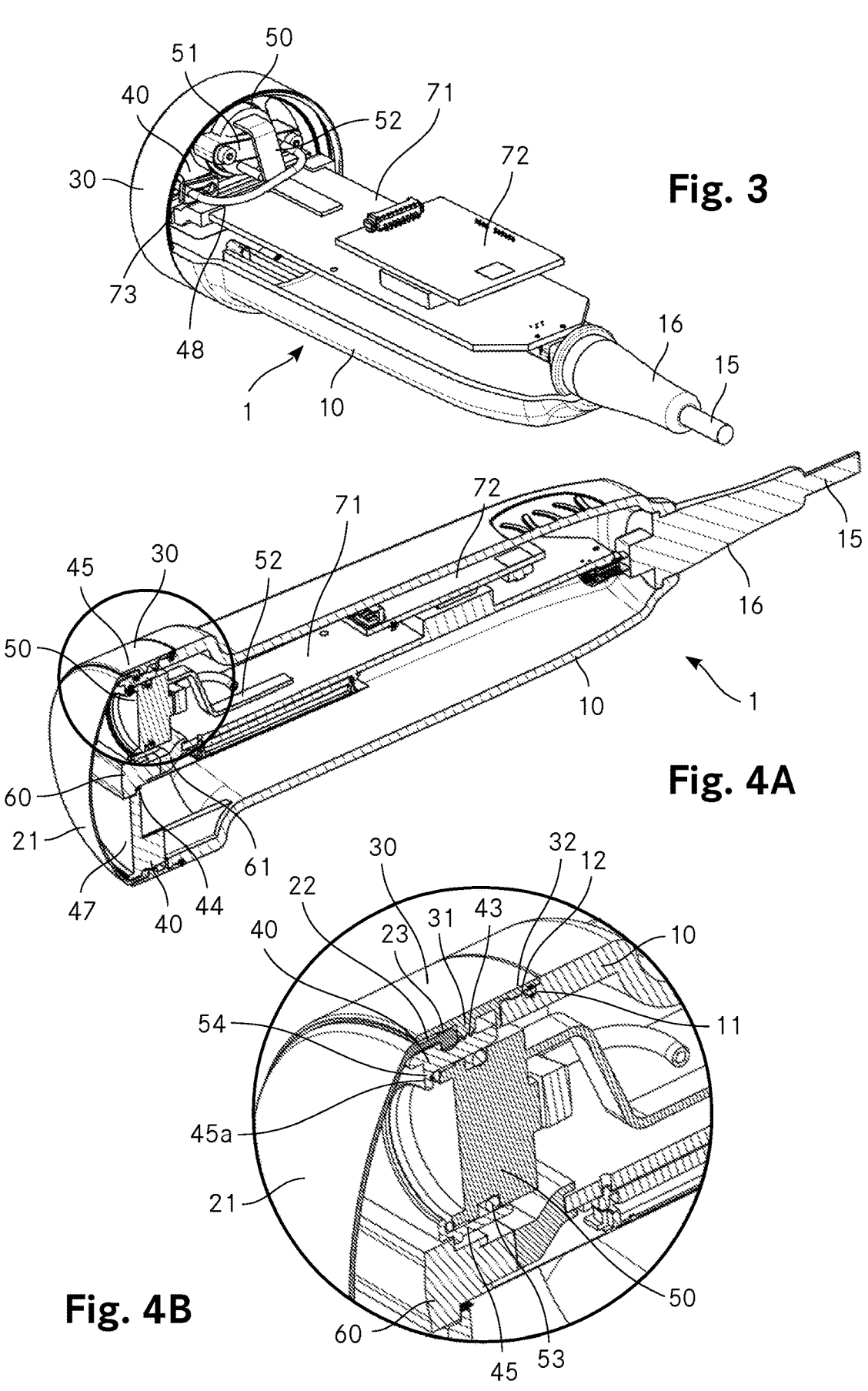
FIG. 3 another oblique view of the device with the housing only partially shown.
FIG. 4A a cut-away diagonal view of the device.
FIG. 4B an enlarged section from FIG. 4A.

FIG. 3 is another oblique view of the device with the housing only partially shown. FIG. 4 shows a cut-away oblique view of the device. A support plate 40 made of anodized aluminum is arranged in the front area of the housing 10, the main surface of which runs transversely to the longitudinal axis of the measuring unit 1. The support plate 40 is shown in FIGS. 6A, 6B. It is circular and comprises a base plate 41 and a jacket 42, on which an external thread 43 is formed. A rectangular opening 44 with rounded corners is arranged in the base plate 41. It extends diametrically over essentially the entire diameter up to a circumferential edge section. A further opening in the base plate 41 opens into a cylindrical receptacle 45, which has a support flange 45*a* flush with the end face. A further opening in the end face of the base plate 41 opens into a channel 46. The support plate 40 accommodates a pressure sensor 50 in the receptacle 45 and an ultrasonic transducer 60 with a piezo array in the opening 44.

The pressure sensor 50 comprises a piezoresistive measuring element that is accommodated in a cylindrical steel housing. The front of the pressure sensor 50 comprises a stainless steel membrane. The pressure acting on it is further transmitted to the measuring element. The pressure sensor 50 has a measuring range of 0-0.35 bar. It provides an amplified analog output signal that can be processed immediately.

A holder 73 for the first printed circuit board 71 is arranged on the rear side of the support plate 71. The pressure sensor 50 is connected to the first printed circuit board 71 via a connection cable 52, which is designed as a flat cable. The ultrasonic transducer 60 is also connected to the first printed circuit board 71 via a further connection cable 61, again a flat cable.

The membrane element 20 (see FIGS. 5A, 5B) is made of silicone rubber with a hardness of 40 Shore A. It is completely circularly symmetrical, has a circular base area with a diameter of approx. 50 mm and has a first, cylindrical area formed by a jacket 22. This has an inwardly projecting bead 23 at the free rear end. The actual membrane 21 is arranged in the front area. The membrane element 20 is also preformed in the area of the actual membrane 21 and, when unfilled, has the shape of a spherical cap with a radius of curvature of 100 mm. With a membrane diameter of approx. 50 mm, this results in a height of 3.1 mm. The geometry avoids excessive lens effects with regard to the transmitted ultrasonic waves and enables good handling in the required angle range.

In the area of the membrane 21, the material thickness is 0.5 mm. In the area of the jacket 22, it is 0.8 mm. Overall, the bead has an essentially circular cross-section with a diameter of 2.0 mm.

As can be seen in particular from FIG. 4B, the jacket 22 of the membrane element 20 interacts with a distal cylindrical region of the support plate 40 in the assembled state. Proximally of this cylindrical region, the support plate 40 has a circumferential recess in which the bead 23 of the membrane element 20 is accommodated. The membrane 21 is supported in the transition area to the jacket 22 by a rounded transition surface of the support plate 40.

The membrane element 20 is secured to the support plate 40 using the stainless steel retaining ring 30. This has an internal thread 31 which interacts with the external thread 43 on the support plate 40. Both proximally and distally of the internal thread 31, the retaining ring 30 has essentially cylindrical sections. The distal section covers the jacket 22 of the membrane element 20 and thus prevents removal of the membrane element 20 due to the interaction of the bead 23 with the recess in the support plate 40. In the section proximal to the internal thread 31, the retaining ring 30 has, on the one hand, an inwardly projecting flange which interacts with an end face of the housing 10. Proximal to the flange, the retaining ring 30 embraces the casing of the housing 10. In this section, proximal to the flange, a circumferential lug 32 is formed on the retaining ring 30, which interacts with a recess 12 in the casing of the housing 10 in the manner of a clip connection. The retaining ring 30 is thus held securely on the housing 10. Furthermore, an O-ring 11 is accommodated in a groove in the outer casing of the housing 10, which, when fitted, interacts with the inside of the proximal section of the retaining ring 30 and seals the interior of the housing against the ingress of moisture and dust.

A sealed chamber 47 for receiving a liquid medium is formed between the support plate 40 and the membrane 21. On the one hand, the sealing takes place between the support plate 40 and the membrane element 20 mounted thereon. On the other hand, the pressure sensor 50 is sealed with respect to its receptacle 45 in the support plate on the one hand by a radially sealing first O-ring 53, which is arranged on the jacket of the pressure sensor 50, and on the other hand by an axially sealing second O-ring 54, which is arranged between an end-face edge section of the pressure sensor 50 and the support flange 45*a* of the receptacle 41.

The ultrasonic transducer 60 is sealed against the support plate 40 by means of adhesive bonding, as described in more detail below.

When mounting the measuring unit 1, the ultrasonic transducer 60 is first attached to the support plate 40. For this purpose, the transducer is inserted from the front into the corresponding opening 44, whereby the contact surfaces between the housing of the ultrasonic transducer 60 and the support plate 40 are first provided with a silicone-based adhesive. After inserting the ultrasonic transducer 60, the bonding area is shaped with a spatula to ensure a reliable seal. Finally, the bonded elements are mechanically fixed together for the drying time of the bond.

Next, a filling hose 48 made of silicone (see FIG. 3) is fed through the channel 46 in the support plate 40 and again fixed in the channel 46 on the front side with a silicone-based adhesive, whereby the end of the hose is aligned with the mouth of the channel 46 on the front side of the base plate 41. Again, the bonding also ensures the seal between the filling hose 48 and the channel 46.

Once the aforementioned bonding has dried, the membrane element 20 can be attached to the support plate 40. For this purpose, it is pulled with its jacket 22 over the jacket 42 of the support plate 40 until the bead 23 of the membrane element 20 comes to lie completely behind the recess in the jacket 42 of the support plate 40. The retaining ring 30 can then be screwed with its internal thread 31 onto the external thread 43 of the support plate 40.

To attach the pressure sensor 50, the first O-ring 54 is first inserted into the receptacle 45 of the support plate 40. It rests on the support flange 45*a*. The pressure sensor 50 with the second O-ring 53 is then inserted into the receptacle 45 from behind until its end face makes contact with the first O-ring 54. A holder 51 (see FIG. 3) can now be placed on the back of the pressure sensor 50 and screwed to the support plate 40 using two screws. The pressure sensor 50 is thereby pressed further forward, onto the first O-ring 54, which creates a secure seal between the pressure sensor 50 and the support plate 40.

The holder 73 for the mainboard is now attached to the ultrasonic transducer 60 and thus to the rear of the support plate 40.

Next, a clamp is pulled over the filling hose 48 and the chamber 47 is filled through the filling hose with a synthetic lubricating oil of viscosity class 46 ISO VG approved for use in the pharmaceutical sector. The weight of the partially mounted sensor including the filled liquid is monitored during filling so that filling can be stopped when a predetermined filling weight is reached. During filling, care is taken to ensure that no air bubbles remain in the chamber 47. The filling hose 48 is then closed by means of the clamp, and the free end of the filling hose 48 is placed on a mandrel, which is arranged on the rear side of the holder 51 for the pressure sensor 50.

Now the first printed circuit board 71 (mainboard) with the printed circuit board 72 (piggyback) held on it can be inserted into the holder 73, creating the connection to the ultrasonic transducer 60 at the same time. The connection cable 52 of the pressure sensor 50 is then connected with its plug to a corresponding socket on the mainboard. The connection cable 15 is also fed through the end opening in the housing 10 and connected to the mainboard with a corresponding plug. The housing 10 is finally connected to the front part (with membrane element 20, retaining ring 30, support plate 40, pressure sensor 50, ultrasonic transducer 60 and the printed circuit boards 71, 72) by pressing it into the retaining ring 30 until the clip connection engages.

The invention is not limited to the embodiment example shown. For example, the geometry of the individual components does not have to correspond to that of the embodiment. For example, the membrane can also be designed with an oval or rounded-rectangular base, which also requires adjustments to other components such as the retaining ring and the housing. The materials can also be selected differently. The chamber does not necessarily have to be sealed with the aforementioned sealing materials either.

In summary, the invention provides a device for carrying out ultrasonic examinations and pressure measurements which is simple in design and enables high image quality.

The invention claimed is:

1. A device for performing ultrasonic examinations and pressure measurements, comprising:
   an ultrasonic transducer;
   a pressure sensor;
   a housing to accommodate the ultrasonic transducer and the pressure sensor;
   a support plate arranged in the housing; and a flexible membrane arranged at a front of the housing;
   wherein
   a sealed chamber for receiving a liquid medium is formed between the flexible membrane and the support plate, and wherein the ultrasonic transducer and the pressure sensor are arranged on the support plate in such a way that a first transmission surface of the ultrasonic transducer and a second transmission surface of the pressure sensor are directed towards the sealed chamber.

2. The device according to claim 1, wherein the flexible membrane has a circular base.

3. The device according to claim 1, wherein a retaining ring is attached to a peripheral retaining region of the support plate and encloses a proximal retaining section of the flexible membrane and holds it on the support plate.

4. The device according to claim 3, wherein the flexible membrane has a bead in the holding section, wherein the bead enters a circumferential groove of the support plate, wherein the circumferential groove is arranged distally in front of the peripheral retaining region.

5. The device according to claim 3, wherein a proximal section of the retaining ring attaches to a shell-side region of the housing in a manner of a clip connection.

6. The device according to claim 5, wherein, a circumferential seal is arranged between the proximal section of the retaining ring and the shell-side region of the housing.

7. The device according to claim 5, wherein the proximal section of the retaining ring attaches to the shell-side region of the housing in a manner of a clip connection.

8. The device according to claim 1, wherein the ultrasonic transducer is attached to a center of the support plate and wherein the pressure sensor is attached off-center to the support plate.

9. The device according to claim 1, wherein the ultrasonic transducer and the pressure sensor are each accommodated in a corresponding through-opening of the support plate, the through-openings with accommodated ultrasonic transducer and pressure sensor being sealed against passage of the liquid medium.

10. The device according to claim 1, wherein the chamber is filled with an ultrasound-transparent liquid.

11. The device according to claim 10, wherein the ultrasonically transparent liquid is an oil with a viscosity in a viscosity class of 32-68 ISO VG.

12. The device according to claim 1, comprising a filling opening for the liquid medium, the filling opening configured as a through-opening in the support plate.

13. The device according to claim 1, wherein a circuit board for holding electronic components is fixed to a rear surface of the support plate, and a main surface of the circuit board extends perpendicular to a main surface of the support plate.

14. A method of assembling a device for performing ultrasonic examinations and pressure measurements, comprising:
   an ultrasonic transducer:
   a pressure sensor;
   a housing to accommodate the ultrasonic transducer and the pressure sensor;
   a support plate arranged in the housing; and
   a flexible membrane arranged at a front of the housing;
   wherein a sealed chamber for receiving a liquid medium is formed between the flexible membrane and the support plate, and wherein the ultrasonic transducer and the pressure sensor are arranged on the support plate in such a way that a first transmission surface of the ultrasonic transducer and a second transmission surface of the pressure sensor are directed towards the sealed chamber,
   the method comprising:
   inserting, sealing and fastening the ultrasonic transducer and the pressure sensor in the support plate;
   inserting a filling hose into the support plate;
   attaching the flexible membrane to the support plate to form the sealed chamber;
   filling the liquid medium into the chamber through the filling hose; and
   closing a filling opening for the liquid medium as soon as a predetermined quantity of the medium has been filled in.

15. The method according to claim 14, wherein a retaining ring is slid over the membrane and fastened to the support plate to form the sealed chamber after the flexible membrane has been attached.

* * * * *